US00PP21257P2

(12) United States Plant Patent
van Haaster

(10) Patent No.: US PP21,257 P2
(45) Date of Patent: Aug. 31, 2010

(54) ***DAHLIA* PLANT NAMED 'FIDAHNEWY'**
(50) Latin Name: *Dahlia hybrida*
Varietal Denomination: Fidahnewy

(75) Inventor: Johanna G. H. van Haaster, De Hillegom (NL)

(73) Assignee: Fides B.V., DeLier (NL)

( * ) Notice: Subject to any disclaimer, the term of this patent is extended or adjusted under 35 U.S.C. 154(b) by 0 days.

(21) Appl. No.: 12/387,028

(22) Filed: Apr. 27, 2009

(51) Int. Cl.
*A01H 5/00* (2006.01)

(52) U.S. Cl. ..... Plt./321

(58) Field of Classification Search ..... Plt./321
See application file for complete search history.

*Primary Examiner*—Susan B McCormick Ewoldt
(74) *Attorney, Agent, or Firm*—C. A. Whealy

(57) ABSTRACT

A new and distinct cultivar of *Dahlia* plant named 'Fidahnewy', characterized by its compact, upright, somewhat outwardly spreading and mounded plant habit; freely branching growth habit; freely flowering habit; large decorative inflorescences with light red purple-colored ray florets; and good postproduction longevity.

1 Drawing Sheet

Botanical designation: *Dahlia hybrida.*
Cultivar denomination: 'FIDAHNEWY'.

BACKGROUND OF THE INVENTION

The present invention relates to a new and distinct cultivar of *Dahlia* plant, botanically known as *Dahlia hybrida,* and hereinafter referred to by the name 'Fidahnewy'.

The new *Dahlia* plant is a product of a planned breeding program conducted by the Inventor in Hillegom, The Netherlands. The objective of the breeding program is to create new pot-type *Dahlia* cultivars that have a freely branching and flowering habit, attractive ray floret coloration and good postproduction longevity.

The new *Dahlia* plant originated from an open-pollination in Hillegom, The Netherlands of an unnamed selection of *Dahlia hybrida,* not patented, as the female, or seed, parent with an unknown selection of *Dahlia hybrida* as the male, or pollen, parent. The new *Dahlia* was discovered and selected by the Inventor as a single flowering plant from within the progeny of the stated open-pollination in a controlled environment in Hillegom, The Netherlands.

Asexual reproduction of the new *Dahlia* plant by cuttings in a controlled environment in Hillegom, The Netherlands since 2006, has shown that the unique features of this new *Dahlia* plant are stable and reproduced true to type in successive generations.

SUMMARY OF THE INVENTION

Plants of the new *Dahlia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Fidahnewy'. These characteristics in combination distinguish 'Fidahnewy' as a new and distinct cultivar of *Dahlia:*

1. Compact, upright, somewhat outwardly spreading and mounded plant habit.
2. Freely branching growth habit.
3. Freely flowering habit.
4. Decorative inflorescences with light red purple-colored ray florets.
5. Good postproduction longevity.

Compared to plants of the female parent selection, plants of the new *Dahlia* differ primarily in ray floret coloration and plant shape.

Plants of the new *Dahlia* can be compared to plants of *Dahlia hybrida* 'Lisa Dark Pink', disclosed in U.S. Plant Pat. No. 11,780. In side-by-side comparisons conducted in De Lier, The Netherlands, plants of the new *Dahlia* differed from plants of 'Lisa Dark Pink' primarily in ray floret color as plants of 'Lisa Dark Pink' had dark pink-colored ray florets.

BRIEF DESCRIPTION OF THE PHOTOGRAPH

The accompanying photograph illustrates the overall appearance of the new *Dahlia* plant. The photograph shows the colors as true as it is reasonably possible to obtain in colored reproductions of this type. Colors in the photograph may differ slightly from the color values cited in the detailed botanical description which accurately describe the colors of the new *Dahlia* plant. The photograph comprises a side perspective view of a typical flowering plant of 'Fidahnewy' grown in a container.

DETAILED BOTANICAL DESCRIPTION

The aforementioned photograph and the following observations and measurements describe plants grown in a glass-covered greenhouse in De Lier, The Netherlands during the late summer and autumn and under conditions and practices which approximate those generally used in commercial *Dahlia* production. During the production of the plants, day and night temperatures averaged 18° C. Measurements and numerical values represent averages for typical flowering plants. Plants were about 10 weeks old when the photograph and description were taken. In the following description, color references are made to The Royal Horticultural Society Colour Chart, Fifth Edition, except where general terms of ordinary dictionary significance are used.

Botanical classification: *Dahlia hybrida* 'Fidahnewy'.

Parentage:

*Female, or seed, parent.*—Unnamed selection of *Dahlia hybrida,* not patented.

*Male, or pollen, parent.*—Unknown selection of *Dahlia hybrida,* not patented.

Propagation:

*Type.*—By cuttings.

*Time to initiate roots, summer.*—About six days at temperatures of about 22° C.

*Time to initiate roots, winter.*—About eight days at temperatures of about 20° C.

*Time to produce a rooted young plant, summer.*—About 12 days at temperatures of about 22° C.

*Time to produce a rooted young plant, winter.*—About 16 days at temperatures of about 20° C.

*Root description.*—Fine, fibrous; tuber development has not been observed.

*Rooting habit.*—Freely branching; dense.

Plant description:

*Plant form/growth habit.*—Upright, somewhat outwardly spreading and mounded plant form; broad inverted triangle; freely basal branching with about five primary branches each with numerous secondary branches and inflorescences held above the foliage on strong peduncles; bushy and dense habit; moderately vigorous growth habit.

*Plant height.*—About 16 cm.

*Plant diameter or spread.*—About 20 cm.

*Lateral branches.*—Length: About 14 cm. Diameter: About 8 mm. Internode length: About 1.5 cm to 2.5 cm. Aspect: Erect to somewhat outwardly spreading. Strength: Moderately strong. Texture: Smooth, glabrous. Color: Close to 144B.

Foliage description:

*Arrangement.*—Leaves opposite; leaves may be single or compound with three or five leaflets.

*Shape.*—Ovate.

*Apex.*—Acute.

*Base.*—Attenuate.

*Margin.*—Serrate.

*Leaflet length.*—About 7 cm.

*Leaflet width.*—About 5 cm.

*Venation pattern.*—Pinnate.

*Texture, upper and lower surfaces.*—Slightly pubescent.

*Color.*—Developing leaves, upper surface: Close to 137A. Developing leaves, lower surface: Close to 138B. Fully expanded leaves, upper surface: Close to N137A; venation, close to 138C. Fully expanded leaves, lower surface: Close to 138B; venation, close to 138B.

*Petioles.*—Length: About 3 cm. Diameter: About 4 mm. Texture, upper and lower surfaces: Smooth, glabrous. Color, upper surface: Close to 144A to 144B. Color, lower surface: Close to 144B.

Inflorescence description:

*Appearance/arrangement.*—Rotate decorative inflorescence form with ray florets forming acropetally on a receptacle; inflorescences positioned above the foliage on strong peduncles; inflorescences face upright to outwardly; freely flowering habit, about 27 inflorescences develop per plant.

*Fragrance.*—None detected.

*Time to flower.*—Plants flower continuously from late spring through the autumn in The Netherlands; plants begin flowering about six to seven weeks after planting.

*Post-production longevity.*—Inflorescences maintain good substance for about two weeks on the plant; inflorescences persistent.

*Inflorescence bud.*—Height: About 4 mm. Diameter: About 5 mm. Shape: Globular, flattened. Color: Close to N144B.

*Inflorescence size.*—Diameter: About 8 cm. Depth (height): About 2.5 cm.

*Ray florets.*—Length: About 2.9 cm. Width: About 1.8 cm. Shape: Oblanceolate. Apex: Obtuse. Base: Cuneate. Aspect: Initially upright to eventually roughly perpendicular to the peduncle. Texture, upper and lower surfaces: Smooth, glabrous. Color: When opening, upper surface: Close to 155D heavily overlain with close to N74A. When opening, lower surface: Close to 155D; towards the center, close to N74A. Fully opened, upper surface: Close to 155D overlain with close to N74A; color does not fade with development. Fully opened, lower surface: Close to 155D, towards the center, close to N74A; color does not fade with development.

*Disc florets.*—None observed.

*Phyllaries.*—Quantity per inflorescence: About five arranged in a single whorl. Length: About 1.4 cm. Width: About 6 mm. Shape: Obovate. Apex: Acute. Base: Cuneate. Margin: Entire. Texture, upper and lower surfaces: Smooth, glabrous. Color, upper and lower surfaces: Close to 137A.

*Peduncles.*—Length: About 7.5 cm. Diameter: About 4 mm. Aspect: Mostly erect. Strength: Strong. Texture: Smooth, glabrous. Color: Close to 144B.

*Reproductive organs.*—Androecium: Quantity per floret: About ten. Filament length: About 1 mm. Filament color: Close to 6C. Anther shape: Narrowly elliptic. Anther length: About 2 mm. Anther color: Close to 17A. Pollen amount: Moderate. Pollen color: Close to N25B. Gynoecium: Not observed. Seeds/fruits: Seed and fruit development have not been observed.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Fidahnewy' as illustrated and described.

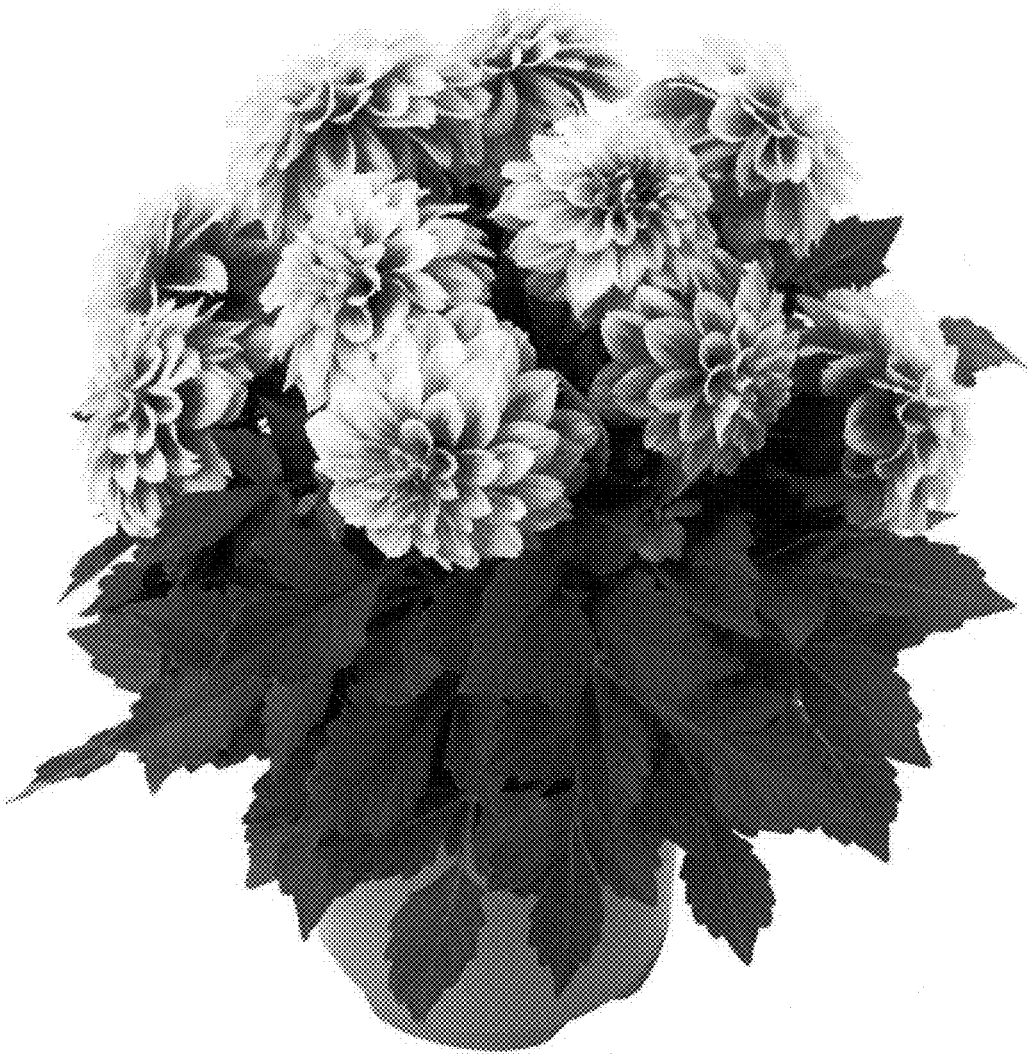

* * * * *